United States Patent
Roman

(10) Patent No.: US 9,993,035 B2
(45) Date of Patent: Jun. 12, 2018

(54) POST SURGICAL BREAST DRESSING

(71) Applicant: EZBRA ADVANCED WOUND CARE LTD., Tel Aviv (IL)

(72) Inventor: Efrat Roman, Tel Aviv (IL)

(73) Assignee: EZBRA ADVANCED WOUND CARE LTD., Tel Aviv (IL)

(*) Notice: Subject to any disclaimer, the term of this patent is extended or adjusted under 35 U.S.C. 154(b) by 33 days.

(21) Appl. No.: 14/368,528

(22) PCT Filed: Dec. 26, 2012

(86) PCT No.: PCT/IL2012/050553
§ 371 (c)(1),
(2) Date: Jun. 25, 2014

(87) PCT Pub. No.: WO2013/098818
PCT Pub. Date: Jul. 4, 2013

(65) Prior Publication Data
US 2015/0141939 A1    May 21, 2015

Related U.S. Application Data

(60) Provisional application No. 61/582,521, filed on Jan. 3, 2012.

(30) Foreign Application Priority Data

Dec. 27, 2011   (IL) .......................................... 217227

(51) Int. Cl.
*A41C 3/00*    (2006.01)
*A61F 13/14*   (2006.01)
(Continued)

(52) U.S. Cl.
CPC .......... *A41C 3/0064* (2013.01); *A61F 13/145* (2013.01); *A61F 13/8405* (2013.01);
(Continued)

(58) Field of Classification Search
CPC ......... A41C 3/005; A41C 3/02; A41C 3/0064; A61F 13/145; A61F 13/8405; A61F 13/14; A61F 13/148; A61F 2013/15016
(Continued)

(56) References Cited

U.S. PATENT DOCUMENTS 2,748,771 A * 6/1956 Richards .................. A41C 3/04
450/36
3,421,514 A * 1/1969 Friedlander .......... A41D 27/136
2/54
(Continued)

FOREIGN PATENT DOCUMENTS

CN          201618006 U    11/2010
DE   10 2006 017 567 A1   10/2007
(Continued)

OTHER PUBLICATIONS

The International Search Report and Written Opinion for PCT/IL2012/050553, five pages, dated Apr. 3, 2013.

*Primary Examiner* — Gloria Hale
(74) *Attorney, Agent, or Firm* — Vorys, Sater, Seymour & Pease LLP

(57) ABSTRACT

Provided is a post surgical breast dressing including: a front portion including a left cup and a right cup connected or connectable to one another; at least one back strap for fitting around a subject's back; left and right trans-axial portions connecting the back strap with the left cup and the right cup, respectively, each of the left and right trans-axial portions including, respectively, left and right in breast in fold portions and left and right under arm portions, the breast dressing wherein at least one of the left under arm portion and right under arm portion include an external layer, an internal layer, and an absorbing dressing.

23 Claims, 4 Drawing Sheets

(51) Int. Cl.
*A61F 13/84* (2006.01)
*A41C 3/06* (2006.01)
*A61F 13/15* (2006.01)

(52) U.S. Cl.
CPC ....... *A41C 3/06* (2013.01); *A61F 2013/15016* (2013.01); *A61F 2013/15081* (2013.01)

(58) Field of Classification Search
USPC ..... 450/58, 86, 88, 93, 61; 604/378, 385.08, 604/385.101, 385.23, 346, 360, 393; 602/79, 53, 61
See application file for complete search history.

(56) References Cited

U.S. PATENT DOCUMENTS

| | | | |
|---|---|---|---|
| 3,968,803 A | 7/1976 | Hyman | |
| 4,369,792 A | 1/1983 | Miller | |
| 4,804,351 A | 2/1989 | Raml et al. | |
| 5,042,089 A * | 8/1991 | Carmer | A41D 27/136 2/55 |
| 5,152,741 A | 10/1992 | Farnio | |
| 5,158,541 A * | 10/1992 | McCurley | A61F 13/145 450/55 |
| 5,395,280 A | 3/1995 | Greenberg | |
| 5,538,502 A | 7/1996 | Johnstone | |
| 5,800,245 A * | 9/1998 | Barbe-Vicuna | A41C 3/0064 2/267 |
| 5,843,018 A * | 12/1998 | Shesol | A61F 13/02 602/41 |
| 5,998,693 A * | 12/1999 | Zagame | A61F 13/145 450/81 |
| 6,203,399 B1 * | 3/2001 | Hackney | A41C 3/00 2/267 |
| 6,258,051 B1 | 7/2001 | Shesol et al. | |
| 6,264,530 B1 * | 7/2001 | Cosentino | A41C 3/12 2/267 |
| 6,348,423 B1 | 2/2002 | Griffiths et al. | |
| 6,390,885 B1 | 5/2002 | Brooks | |
| 6,786,798 B1 * | 9/2004 | Gendel | A41C 3/02 450/1 |
| 7,619,130 B2 | 11/2009 | Nielsen et al. | |
| 2002/0143304 A1 * | 10/2002 | Elder | A61F 13/51305 604/360 |
| 2004/0058619 A1 * | 3/2004 | Spiezio | A61F 13/141 450/57 |
| 2005/0004501 A1 * | 1/2005 | Lorenzo | A61F 5/03 602/75 |
| 2005/0229935 A1 * | 10/2005 | Khalaf | A41C 3/0064 128/845 |
| 2007/0275635 A1 | 11/2007 | Pitarelli | |
| 2009/0299252 A1 * | 12/2009 | O'Neill | A61F 13/145 602/48 |
| 2010/0022164 A1 * | 1/2010 | Taylor | A41C 3/10 450/41 |
| 2010/0101585 A1 | 4/2010 | Frye | |
| 2010/0101586 A1 * | 4/2010 | Frye | A61F 13/145 128/889 |
| 2010/0130098 A1 | 5/2010 | Kammerer | |

FOREIGN PATENT DOCUMENTS

| | | |
|---|---|---|
| JP | 7-3655 U | 1/1995 |
| JP | 2007-332520 A | 12/2007 |
| WO | 2007/092350 A1 | 8/2007 |
| WO | 2007/118580 A1 | 10/2007 |

* cited by examiner

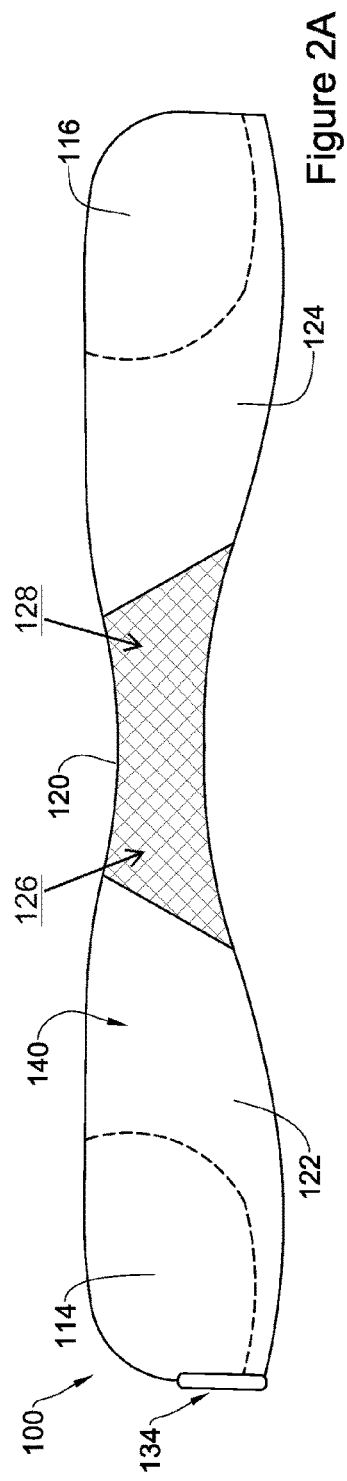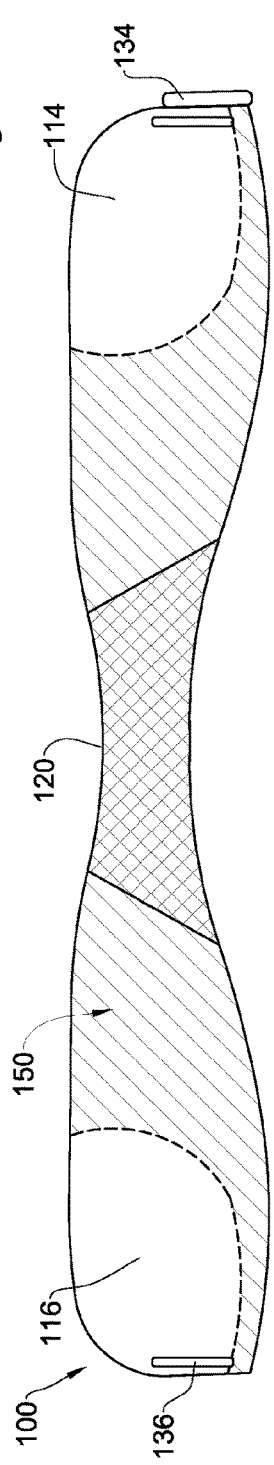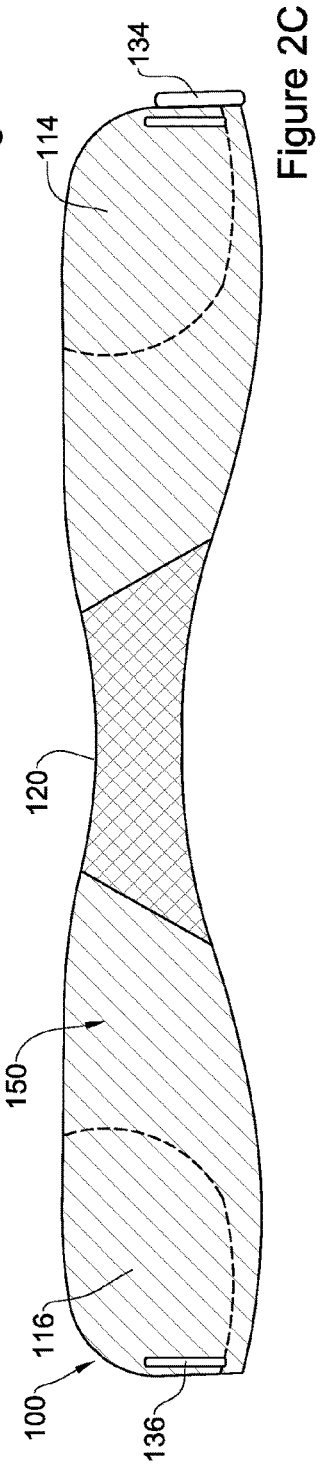

POST SURGICAL BREAST DRESSING

FIELD OF THE INVENTION

This invention relates to post surgical brassieres.

BACKGROUND OF THE INVENTION

Breast surgery including medical and cosmetic surgeries involves surgical intervention in the breast and nearby regions. Cosmetic surgery may include, for example, breast reduction surgery, augmentation mammoloplasty, mastopexy or breast lift surgery. Medical breast surgery may include, for example, lumpectomy, and mastectomy.

Mastectomy is surgery to remove a breast, either to treat or to prevent breast cancer. There are four main types of mastectomy: Total mastectomy (removal of breast tissue and nipple); Modified radical mastectomy (removal of the breast, most of the lymph nodes under the arm and often the lining over the chest muscles); Lumpectomy (surgery to remove the tumor and a small amount of normal tissue around it); and Radical mastectomy (the removal of the breast, lymph nodes and chest muscles).

After a mastectomy, a patient may use a prosthetic device to provide symmetry to their body, in case there is no breast reconstitution. Such prosthetic devices are made with a specially designed pocket in each cup and silicone breast forms slipped inside the relevant pocket, where it is held firmly in place against the body for a natural recreation of symmetry. Designed especially for this purpose, a mastectomy bra may also be made with features similar to traditional bras, such as both front or back hook closures and a choice of satin, lace, or cotton. An example of a prosthetic device is described in U.S. Pat. No. 6,390,885 which includes, in addition to the prosthetic elements, also a fluid drainage system for removal of fluids after breast surgery.

In addition, post surgery breast or chest bandages or recovery devices are known, irrespective of whether a breast or part thereof was removed and reconstituted. For example, U.S. Pat. No. 5,152,741 describes a surgical chest dressing constructed of a chest encircling flexible band formed from a stretchable material and different support structures.

In addition, US Patent Application Publication No. 2007/0275635 describes a post surgical medical device tightened about a patient's thorax using bandage bands that cross the patient's thorax many times, to give proper containment of the device without the need of adhesive tapes.

Finally, Japanese Patent Application Publication No. JP2007332520 describes a post surgical brassiere with means for cooling a patient's breasts or armpits for reducing swelling during or after radiation therapy.

SUMMARY OF THE INVENTION

The present invention is based on the design of a new post surgical wound dressing particularly suitable for women after breast surgery, such as, for example, mastectomy.

The breast dressing, in accordance with the present disclosure comprises:
1. a front portion comprising a left cup and a right cup connected or connectable to one another;
2. at least one back strap for fitting around a subject's back, the back strap comprising, respectively, a left end and a right end;
3. left trans-axial portion and right trans-axial portion connecting the left end of the back strap with the left cup and the right end of the back strap with the right cup, respectively, the left trans-axial portion and the right trans portion comprising, respectively, left and right in breast fold portions and left and right under arm portions;

wherein at least one of the left under arm portion and right under arm portion comprise an external layer, an internal layer and an absorbing dressing.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 2A-2C are back (FIG. 2A) and front (FIGS. 2B, 2C) elevational views, in flattened condition, of a post surgical breast dressing as illustrated in FIGS. 1A and 1B, albeit in open configuration;

DETAILED DESCRIPTION OF SOME NON LIMITING EMBODIMENTS

Figure 1A:
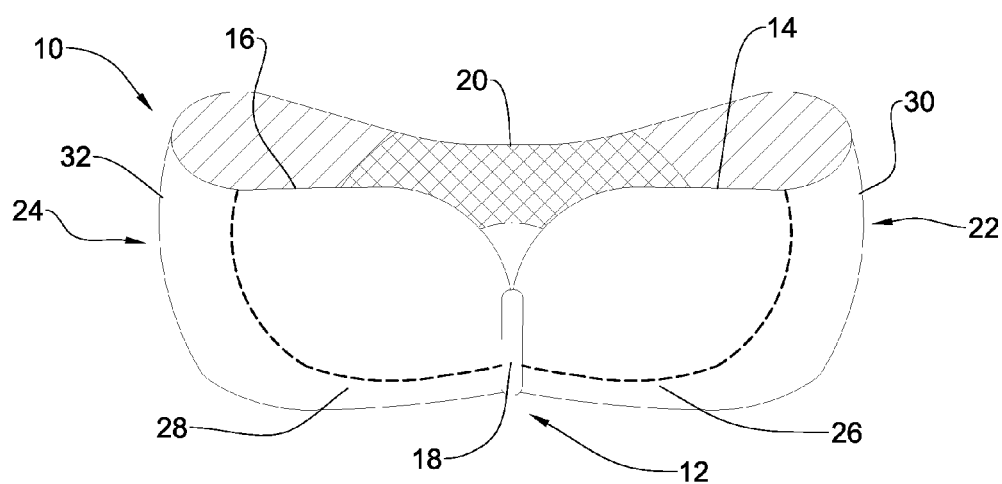
FIGS. 1A and 1B are respectively, front (FIG. 1A) and back (FIG. 1B) perspective views of a post surgical breast dressing in accordance with one embodiment of the invention.

The present invention concerns a post surgical breast dressing and specifically a wound dressing for a breast that has a unique design providing, inter alia, a solution to excessive exudates or other fluids exerted from post surgical incisions at the trans-axial portions of the breast.

Specifically, the inventors have realized that after breast surgery, not only the breast cup or the nipples portion per se require gentle care (e.g. gentle dressing) but also the inframammary breast fold, located under the breast, and the area under the arms, collectively referred to as the trans-axial portions of the breast (left trans-axial and/or right trans-axial portions of the breast).

The inventors have appreciated that the left trans-axial and/or right trans-axial portions of the breast, are severely affected (injured) following breast surgery. For example, these portions of the breast have a tendency to leak exudates from the scissions area, to show redness and be swollen, and also to develop infections.

Accordingly, the inventors have developed a solution that provides wound dressing to the trans-axial portions of the breast which is simple and devoid of the discomfort and health risks provided by conventional drainage devices. Due to its simplicity, the breast dressing according to the present disclosure may also be provided as a sterile dressing.

As such, in accordance with its first aspect, the present disclosure provides a post surgical breast dressing comprising a front portion comprising a left cup and a right cup connected or connectable to one another; at least one back strap for fitting around a subject's back; left and right trans-axial portions connecting the back strap with the left cup and the right cup, respectively, each of the left and right trans-axial portions comprising, respectively, left and right in breast fold portions and under arm portions; wherein at least one of the left trans-axial portion and right trans-axial portion comprise an external layer and an internal layer comprising an absorbent wound dressing.

As used herein the terms "left trans-axial portion" and "right trans-axial portion" refer to an anatomical region that comprises at least the transaxial body area under the respectively, left and right arms. In some embodiments, the left trans-axial portion and right trans-axial portion comprise the inframammary fold and the transaxial area under the respectively, left and right sides of the breast and arms.

The inframammary fold (IMF) also known as inframammary crease or inframammary line is a feature of human anatomy being a natural boundary of a breast from below, the place where the breast and the chest meet. The term "trans-axial", as used herein refers to the underarm area. In breast surgery, an incision is made in the transaxial portion. The aim of the dressing disclosed herein, among others, is to avoid the need of using the uncomfortable and less safe solutions in the form of drainage tubes, such as the Jackson-Pratt drain (JP drain, a surgical drainage device for pulling excess fluid from the body by constant suction) in order to treat wounds at the trans-axial portions of a subject's breast.

Taking into consideration that the sensitivity of the trans-axial portions may continue at least a few days and even more after surgery, the inventors have envisaged a novel and inventive design of a bra-like, absorbing wound dressing. The breast dressing comprise a dedicated bandage (referred as a wound dressing) at least at the trans axial areas of the breast, if not the entire trans-axial portions, to thereby reduce discomfort, pain and medical risks of infection at these areas.

Figure 1B:
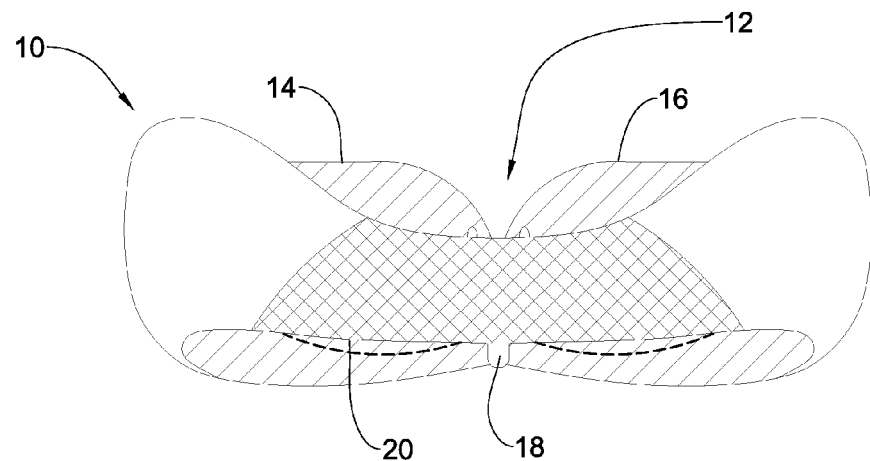

Reference is now made to FIGS. 1A and 1B showing a schematic illustration of a breast dressing according to one embodiment of the invention with FIG. 1A, providing a front perspective view of the breast dressing 10 and FIG. 1B, providing a back view of the breast dressing 10 of FIG. 1A. For simplicity, the same elements of the breast dressing in FIG. 1A are also used in FIG. 1B.

Specifically, breast dressing 10 comprises a front portion 12 comprising a left cup 14 and a right cup 16.

When referring to a "cup" it is to be understood as meaning a dressing portion having a hemispherical shape that can overlay a breast of a subject. The cup may vary in dimensions (diameter, depth, concavity etc.). In the context of the present disclosure, and as will be further discussed below, left cup 14 and a right cup 16 may be the same or different in dimensions.

In some embodiments, the left cup and right cup dimensions are similar. In some embodiments, the left cup and right cup dimensions are symmetrical. In some other embodiments, the left cup and right cup dimensions are asymmetrical.

According to some embodiments, each of trans-axial under arm and right trans-axial under arm portions, and at times also the breast fold areas and/or cups comprise an external layer and an internal layer.

In some embodiments, the absorbing dressing is part of the internal layer or constitutes the internal layer.

When referring to an external and an internal layer, it should be understood that the side of the dressing in contact with the body is termed an internal layer and the side that is not in contact with the body is termed an external layer. Thus, the internal layer may also be regarded as a body facing layer.

In some embodiments, the left cup 14 and a right cup 16 are connected to one another in at least one connection point 18.

Figure 1C:
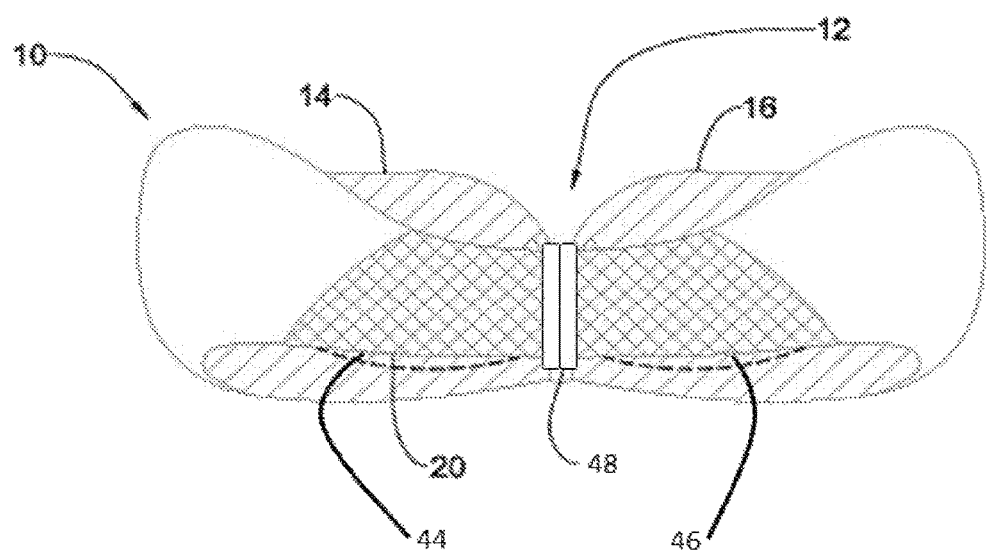
FIG. 1C is a back perspective view of a post surgical breast dressing in accordance with one embodiment of the invention.

Reference is now made to FIG. 1C showing a schematic illustration of a breast dressing according to one embodiment of the invention. The breast dressing 10 includes a front portion 12 having a left cup 14 and a right cup 16. The breast dressing 10 further includes a back strap 20 for fitting around a subject's back. The back strap 20 includes a left back portion 44 and a right back portion 46 that are selectively connected to each other by an adjustable attachment element 48.

Further, as part of breast dressing 10, there is a back strap 20 for fitting around a subject's back (not illustrated); a left trans-axial portion 22 and right trans-axial portion 24 connecting back strap 20 with left cup 14 and right cup 16, respectively.

Each of left trans-axial portion 22 and right trans-axial portion 24 comprises left in breast fold portion 26 and right in breast fold portion 28 and left under arm portion 30 and right under arm portion 32.

The post surgical breast dressing 10 is characterized in that at least one of left trans-axial portion 22 and right trans axial portion 24 comprise an external layer and an internal layer which are illustrated in FIGS. 1A and 1B, providing the breast dressing open, flattened configuration.

For simplicity, like reference numerals to those used in FIG. 1A or 1B, shifted by 100, are used in FIGS. 2A-2C to identify components having a same or similar function. For example, component 114 in FIG. 2A is a left cup having the same function as left cup 14 in FIG. 1A.

Specifically, back elevational view of breast dressing 100 is shown to include a left cup 114 and a right cup 116 and a back strap 120. Back strap 120 comprises a left back portion 126 and a right back portion 128. Both the left back portion 126 and right back portion 128 are integrally formed with the left trans-axial portion 122 and right trans-axial portion 124 to form a continuous left and right, respectively.

Left cup 114 and right cup 116 have in the illustrated embodiments of FIGS. 1A-1B and 2A-2C the same size and shape. However, in accordance with some embodiments, the left cup and the right cup may be of different dimensions. For example, when a subject undergoes reconstruction (medical or cosmetic) of only one breast. In such a situation, the untouched breast may be overlaid with a cup with minimal concavity or may have no concavity (e.g. flat).

As detailed above, left cup 114 and right cup 116 are connectable to each other in at least one connection point. In some embodiments, the connection is by a two part connecting element comprising a first part 134 and a second part 136 operable to allow enclosure of the dressing between the subject's left and right breasts.

The term "connecting element" is used in the context of the present disclosure to denote a physical element that maintains the two ends sides of an opening in a dressing material in a close form. In some embodiments, the connecting element enables the closure between left cup 114 and right cup 116.

In some embodiments, left cup 114 and right cup 116 are connectable to each other by an adjustable attachment element, e.g. a fastener comprising hooks and a series of eyes (loops) to which the hook may fit or the arrangement may be in the form of VELCRO® (a hook and loop fastening system) strap, snap fastener etc. The adjustability allows manipulating the distance between the two cups according to need.

In some embodiments, the connecting element may be a type of fastener.

The term "fastener" is used to denote any special closing devices. In some embodiments, the fastener may be fastened and unfastened repeatedly and upon need.

The fastener may include, without being limited thereto, buckle, hook and loop (VELCRO®), press studs (snap fasteners), adhesive tapes or knot type fastener.

In some embodiments, the breast dressing 100 comprises an external layer 140 (FIG. 2A), and an internal layer 150 (FIG. 2B) in at least the left trans-axial portion 122 and/or right trans axial portion 124.

In some embodiments, the external layer comprises a fluid impermeable material. In some embodiments, the internal layer 150 (FIG. 2B) comprises a dressing material.

At times, also left cup and right cup 114, 116, respectively, may include an external fluid impermeable layer and internal dressing layer 150 as illustrated in FIG. 2C.

Accordingly, each of the left back portion 126, left trans-axial portion 122, and left cup 114, as well as the right back portion 128, right trans-axial portion 124 and right cup 116 are integrally formed as a unit with a continuous left and right, respectively, external and internal layers.

Back strap 120 in breast dressing 100 may comprise an elastic material as well as a non elastic material or any combination of same.

In some embodiments, the breast dressing comprises an elastic material. Non-limiting examples of elastic material include one or a combination of polyurethane, polyester, rubber (e.g. synthetic rubber) and nylon.

Upon use, internal layer 140 is overlaid onto a subjects' skin where the dressing while external layer 150 is exposed outwardly. The external layer 150 may be a combination of any one of an elastic or non-elastic material with stretchable or non stretchable material. In accordance with some embodiments, external layer 150 is composed of a non-stretchable, non-elastic material. In some other embodiments, the external layer has some elasticity to an extent that in allows holding the dressing in place over the wound, without causing any discomfort to the patient.

In some embodiments, the material from which each of the layers, independently, are formed, are materials commonly used in the textile industry, and in some embodiments, in the bra manufacturing arena. The layers may comprise the same or different materials.

It the context of the present disclosure it is to be understood that a stretchable material is one that would conform to the body contour which it overlays without exerting substantial pressure. An elastic material is one that would conform to the body contour which it overlays but will exert a pronounced pressure on the surface because of its tendency to return to its original shape. The return force of a stretchable material is very small when compared to that of an elastic material. Thus, material is such that would conform to the shape of the body it overlays, without applying any inconvenient pressure onto the body.

In accordance with some embodiments, the external layer is a non-woven fabric, including any natural or synthetic non-woven fabric.

The dressing in internal layer 140 is, in accordance with some embodiments, comprise absorbent dressing. As appreciated, the absorbent dressing is configured such as to be placed on post surgical incisions.

In some other embodiments the internal layer comprises a wound dressing. The wound dressing in accordance with the present disclosure is of a kind that absorbs exudates or other fluids exerted from post surgical incisions upon which internal layer is superimposed, namely, comprises an absorbing material.

The term "dressing" or specifically "wound dressing" used herein is taken to include any physiologically acceptable wound covering or support matrix such as:

a) Films, including those of a semipermeable or a semi-occlusive nature such as polyurethane copolymers, acrylamides, acrylates, paraffin, polysaccharides, cellophane and lanolin.

b) hydrocolloids including carboxymethylcellulose protein constituents of gelatin, pectin, and complex polysaccharides including Acacia gum, guar gum and karaya. The hydrocolloid material may be used in the form of a flexible foam or, in the alternative, formulated in polyurethane or, in a further alternative, formulated as an adhesive mass such as polyisobutylene.

c) hydrogens such as agar, starch or propylene glycol; which typically contain about 80% to about 90% water and are conventionally formulated as sheets, powders, pastes and gels in conjunction with cross-linked polymers such as polyethylene oxide, polyvinyl pyrollidone, acrylamide, propylene glycol.

d) Foams such as polysaccharide which consist of a hydrophilic open-celled contact surface and hydrophobic closed-cell polyurethane.

e) Impregnates including pine mesh gauze, paraffin and lanolin-coated gauze, polyethylene glycol-coated gauze, knitted viscose, rayon, and polyester.

f) cellulose-like polysaccharide such as alginates, including calcium alginate, ammonium alginate, which may be formulated as non-woven composites of fibers or spun into woven composites.

In some embodiments, the wound dressing is inert to the body and does not cause irritations and the like.

In one embodiment, the wound dressings are polysaccharide-containing support matrices which may be derivatized with silver or copper and/or have silver alginate bound to or placed upon them (e.g., cross-linked or in a form other than silver alginate) and may also include chitosans, alginates and cotton or carboxymethylated cotton in the form, of gauze, films, hydrocolloide, hydrogels, hydroactives, foams, impregnates, absorptive powders and pastes. In some embodiments, the wound dressing includes a cotton cellulose gauze formed as a woven or nonwoven.

In accordance with some embodiments, the internal layer or a portion thereof also comprise an active substance effective to improve healing of the subject after breast surgery. When referring to improvement of healing it is to be understood as encompassing both treatment of a medical condition so as to eliminate the medical condition but also to reduce its severity; as well as prevention of a medical condition from occurring. The medical condition may include, for example, tissue damage (e.g. due to the incision), irritation, infection, pain at the area of incisions, redness, swollen tissue.

In some embodiments, the substance may be, an approved drug, transition metals, herb (e.g. herb extracts), vitamins (e.g. vitamin B, vitamin C, vitamin E), biological proteins such as enzymes and growth factors (e.g. for promoting collagen regeneration), biological adhesives (e.g. collagen-based, fibrin-based glues) etc.

For example, the drug may be selected from antibiotics, antiseptics, analgesics. Herbal medicine may also be taken into consideration, such as the inclusion of Aloe Vera, Dandelion (Pu GongYing), Anemarrhena (Zhi Mu), calendula etc., known to be beneficial for post radiation treatment; *Panax pseudoginseng* (San Qi-Tian Qi), *Arnica* (also known as Leopard's bane or Mountain tobacco), known to be beneficial for post surgical recovery; Barbat skullcap (Ban Zhi Lian), Anemarrhenae asphodeloides (Zhi Mu), rhubarb root (Da Huang), known to be beneficial against cancer.

In some embodiments, the substance may be a transitional metal. For example, zinc, copper or silver are known for their antimicrobial or anti-inflammatory effect. Also, copper is known to be beneficial as a stimulant for the production of hemoglobin (red blood cells), and other key proteins that help stabilize skin layers, for promoting wound healing, zinc and copper are also known to be beneficiary for collagen synthesis.

Internal layer 140 may be impregnated and/or coated with the active substance and once in contact with the skin or with fluid from an incision, the substance may be released from the internal layer onto the subject's skin and onto the incision with which it is brought into contact.

At times, the active substance may be incorporated in a controlled release delivery formulation, such as micro or nanocapsules, liposomes, micro or nanospheres, micro or nanoemulsions etc., as known in the art. The controlled release may include slow release, conditional release (e.g. only if the incision secrets fluids).

In some embodiments, the internal layer 140 and external layer 150 are fixedly attached to each other. This may be achieved by welding techniques, by the use of adhesives (chemical adhesives as well as biological adhesives). The attachment may be at selected areas or points, or through their entire interface (not shown).

Figure 3:
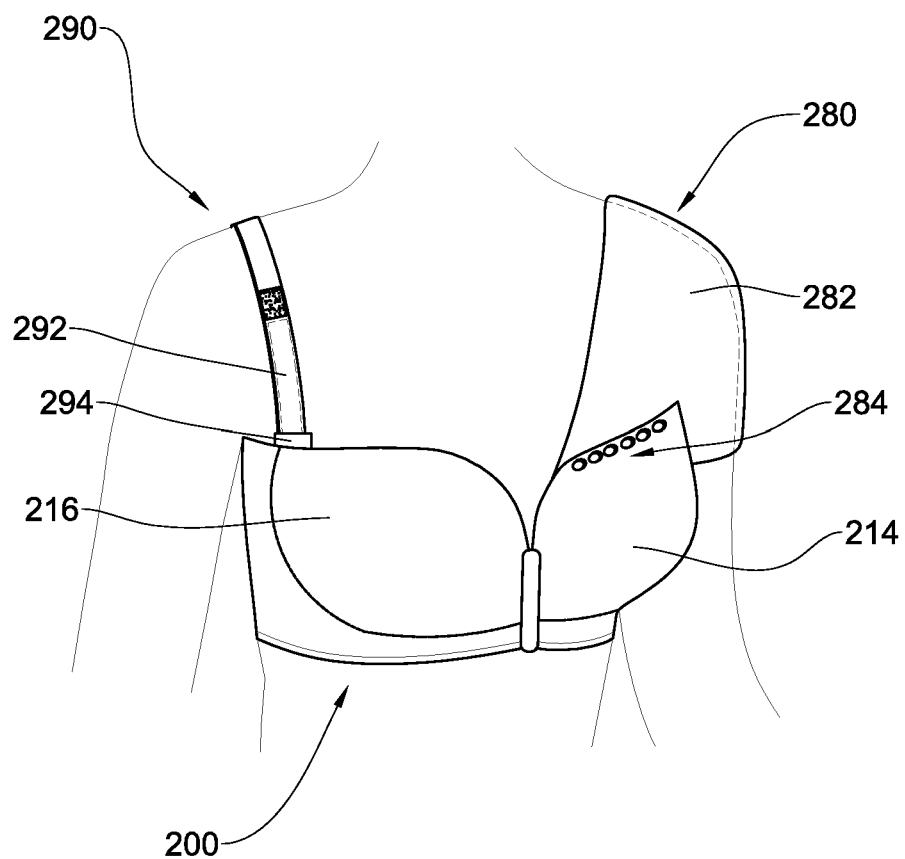
FIG. 3 is schematic illustration of a dressing according to some embodiments of the invention, worn on a subject.

Reference is now made to FIG. 3. For simplicity, like reference numerals to those used in FIG. 1A or 1B, shifted by 200, are used in FIG. 3 to identify components having a same or similar function. For example, component 14 in FIG. 1A is a left cup having the same function as left cup 214 in FIG. 3.

Specifically, FIG. 3 is a front view of a breast dressing 200 worn on a subject. Breast dressing 200 comprises a left shoulder portion 280 and a right shoulder portion 290, being in the illustrated embodiment, different. Specific to this non-limiting embodiment, left shoulder portion 280 comprise a sleeve 282 to cover the subjects shoulder and portion of the arm. Sleeve 282 would preferably be made of a synthetic or natural fabric typically used in clothing, such as cotton, silk, polyester, etc. Right shoulder portion 290 is comprise a length adjustable strap 292, the adjustable attachment element inter-engages a fastener, such as a VELCRO® strap, for varying the effective length of said strap. The shoulder portions may be fixedly or releasably secured to the back strap (not illustrated) and, respectively, to one or both of the left and to the right cups. In the illustrated embodiment of FIG. 3, Sleeve 282 is releasably connected to cup 214 by a series of snap fasteners 284, while length adjustable strap 292 is releasably connected to cup 216 by loop 294.

In some embodiments, the left and right shoulder portions are in the form of adjustable straps and the straps may be connected to the left and right cups in cross configuration, namely, left shoulder strap is connected to right cup and right shoulder strap is connected to left cup, so as to form an "X" arrangement of the straps at the back of the subject. This may be advantageous for ensuring that the dressing is firmly secured in place.

In some further embodiments, the adjustable shoulder straps are non elastic, non-stretchable. The shoulder straps may include a soft foam material disposed between the non elastic, non stretchable materials.

In some other embodiments, the adjustable shoulder straps are made of a material that has some but not high degree of elasticity.

In some embodiments, the shoulder portions are formed from materials commonly used in the textile industry, and in some embodiments, in the bra manufacturing arena.

In accordance with some preferred embodiments, the post surgical breast dressing disclosed herein is made of disposable materials. In other words, the dressing is a disposable dressing for essentially single use by the subject at any time after surgery (immediately after as well as several days or weeks after surgery).

In accordance with some embodiments, the post surgical breast dressing is a sterile breast dressing. To this end, as a step in its manufacturing, the dressing undergoes a sterilization process, and is hermetically sealed within a package.

The invention has been described with reference to some embodiments and its apparent that many modifications can be incorporated into the design and assembly of the post surgical dressing disclosed herein without departing from the essence of the invention, as defined in the claims.

The invention claimed is:

1. A post surgical breast dressing, comprising:
a front portion comprising a left cup and a right cup connected or connectable to one another;
at least one back strap for fitting around a subject's back, the back strap comprising, respectively, a left back portion and a right back portion; and
a left trans-axial portion and right trans-axial portion connecting the left back portion of the back strap and the right back portion of the back strap with the left cup and the right cup, respectively, the left trans-axial portion and the right trans-axial portion comprising, respectively, left in breast fold portion and right in breast fold portion and left under arm portion and right under arm portion, each of the left in breast fold portion and right in breast fold portion of the post surgical breast dressing extending horizontally below substantially all of the respective left and right cup;
wherein at least one of the left in breast fold portion and the right in breast fold portion comprise an external layer, an internal layer and an absorbing dressing.

2. The post surgical breast dressing of claim 1, wherein the internal layer comprises the absorbing dressing.

3. The post surgical breast dressing of claim 1, wherein the external layer comprises a fluid impermeable material.

4. The post surgical breast dressing of claim 1, wherein the left trans-axial portion and cup, and the right trans-axial portion and cup integrally form, respectively, a continuous left external layer and left internal layer and a continuous right external layer and right internal layer.

5. The post surgical breast dressing of claim 1, wherein the internal layer is the absorbent dressing and the absorbent dressing is in position to be placed on post surgical incisions.

6. The post surgical breast dressing of claim 5, wherein said absorbent dressing comprises a liquid absorbing substance for absorbing exudates exerted from post surgical incisions.

7. The post surgical breast dressing of claim 1, wherein at least a portion of the internal layer comprises a substance effective to improve healing of a wound after breast surgery.

8. The post surgical breast dressing of claim 7, wherein the substance is selected from the group consisting of antibiotics, antiseptic, analgesics, herbal medicine, transition metals, vitamins, and biological proteins for release onto post surgical incisions.

9. The post surgical breast dressing of claim 8, wherein the substance is formulated in a conditional release delivery formulation that releases when the substance is in contact with fluid.

10. The post surgical breast dressing of claim 8, wherein the substance is formulated in a controlled release delivery formulation.

11. The post surgical breast dressing of claim 1, wherein the external layer and internal layer are fixedly attached to each other.

12. The post surgical breast dressing of claim 1, comprising symmetrical or asymmetrical left and right cup dimensions.

13. The post surgical breast dressing of claim 1, wherein the left cup and right cup are connectable to each other by an adjustable attachment element.

14. The post surgical breast dressing of claim 1, wherein the left back portion and the right back portion are connectable to each other by an adjustable attachment element.

15. The post surgical breast dressing of claim 1, comprising a left shoulder portion and a right shoulder portion, fixedly or releasably secured to said back strap and, respectively, to one or both of the left and to the right cups.

16. The post surgical breast dressing of claim 15, wherein the left shoulder portion and right shoulder portion are in the form of a strap or a sleeve.

17. The post surgical breast dressing of claim 16, wherein the left shoulder portion and right shoulder portion are fixedly connected to the back strap and releasably secured to each of the left and right cups.

18. The post surgical breast dressing of claim 17, wherein the left and right shoulder portions are releasably secured to said left and right cups by an adjustable attachment element.

19. The post surgical breast dressing of claim 1, being a disposable breast dressing.

20. The post surgical breast dressing of claim 1, being a sterile breast dressing.

21. The post surgical breast dressing of claim 1, wherein the back strap portion comprises an elastic material.

22. The post surgical breast dressing of claim 1, wherein the left in breast fold portion and the right in breast fold portion extends horizontally below all of the respective left and right cup.

23. The post surgical breast dressing of claim 22, wherein the left in breast fold portion and the right in breast fold portion extend horizontally to a connection point at which the left cup and right cup are connected or connectable to one another.

* * * * *